US009642351B1

(12) United States Patent
Reese

(10) Patent No.: US 9,642,351 B1
(45) Date of Patent: May 9, 2017

(54) COCKROACH BAIT STATION

(71) Applicant: Kenneth Reese, Freeport, NY (US)

(72) Inventor: Kenneth Reese, Freeport, NY (US)

( * ) Notice: Subject to any disclaimer, the term of this patent is extended or adjusted under 35 U.S.C. 154(b) by 0 days.

(21) Appl. No.: 15/263,806

(22) Filed: Sep. 13, 2016

(51) Int. Cl.
*A01M 1/20* (2006.01)
*A01M 1/14* (2006.01)
*A01M 1/02* (2006.01)
*A01N 59/14* (2006.01)

(52) U.S. Cl.
CPC ............ *A01M 1/2011* (2013.01); *A01M 1/02* (2013.01); *A01M 1/14* (2013.01); *A01N 59/14* (2013.01)

(58) Field of Classification Search
CPC  A01M 1/00; A01M 1/02; A01M 1/10; A01M 1/14; A01M 1/20; A01M 1/2005; A01M 1/2011
USPC .............................. 43/131, 121, 114
See application file for complete search history.

(56) References Cited

U.S. PATENT DOCUMENTS

| 149,918 | A | | 4/1874 | Clough | |
|---|---|---|---|---|---|
| 554,616 | A | * | 2/1896 | Cook | 43/121 |
| 1,024,767 | A | | 4/1912 | Dempster | |
| RE14,782 | E | * | 12/1919 | Hedrich | 43/131 |
| RE16,949 | E | * | 5/1928 | Gaskins, Jr. | A01M 1/2005 43/131 |
| 1,734,818 | A | | 10/1928 | March | |
| 2,054,730 | A | * | 9/1936 | Pierpoint | A01M 1/10 43/121 |
| 2,291,358 | A | * | 7/1942 | Treadwell | A01K 97/04 43/131 |
| 2,328,590 | A | * | 9/1943 | Weil | A01M 1/2005 43/131 |
| 2,328,591 | A | * | 9/1943 | Weil | A01M 1/2005 43/131 |
| 2,340,255 | A | * | 1/1944 | Weil | A01M 1/2005 43/131 |
| 3,913,259 | A | * | 10/1975 | Nishimura | A01M 1/02 43/114 |
| 3,940,874 | A | * | 3/1976 | Katsuda | A01M 1/14 43/114 |
| 3,965,609 | A | * | 6/1976 | Jordan | A01M 25/004 43/131 |
| 4,031,654 | A | * | 6/1977 | Gray | A01M 1/14 43/114 |
| 4,044,495 | A | * | 8/1977 | Nishimura | A01M 1/02 43/114 |
| 4,048,747 | A | * | 9/1977 | Shanahan | A01M 1/02 43/114 |
| 4,208,828 | A | * | 6/1980 | Hall | A01M 1/02 43/121 |

(Continued)

FOREIGN PATENT DOCUMENTS

| JP | 07298818 | A | * | 11/1995 |
|---|---|---|---|---|
| JP | 11004646 | A | * | 1/1999 |

(Continued)

*Primary Examiner* — Darren W Ark

(57) ABSTRACT

The cockroach bait station is an eradication system that is adapted for use with cockroaches. The cockroach bait station is comprises a bait and a bait station. The bait is a high energy, and therefore highly attractive, bait source that is laced with a poison that is known to be effective in: 1) limiting the future activities of cockroaches after ingestion; and, 2) is readily shared and transferred within a community of cockroaches.

10 Claims, 4 Drawing Sheets

(56) References Cited

U.S. PATENT DOCUMENTS

| | | | | |
|---|---|---|---|---|
| 4,217,722 A * | 8/1980 | McMullen | A01M 1/14 | 43/114 |
| 4,244,134 A * | 1/1981 | Otterson | A01M 23/005 | 43/114 |
| 4,364,194 A * | 12/1982 | Clark, Sr. | A01M 25/004 | 43/131 |
| 4,395,842 A * | 8/1983 | Margulies | A01M 1/02 | 43/114 |
| 4,400,904 A * | 8/1983 | Baker | A01M 25/004 | 43/131 |
| D275,124 S | 8/1984 | Carlsen | | |
| 4,541,198 A * | 9/1985 | Sherman | A01M 25/004 | 43/131 |
| 4,608,774 A * | 9/1986 | Sherman | A01M 1/02 | 43/114 |
| 4,630,392 A * | 12/1986 | Ferraro | A01M 25/004 | 43/131 |
| 4,648,201 A * | 3/1987 | Sherman | A01M 25/004 | 43/131 |
| 4,658,536 A * | 4/1987 | Baker | A01M 25/004 | 43/131 |
| 4,696,127 A * | 9/1987 | Dobbs | A01M 1/02 | 43/114 |
| 4,709,503 A * | 12/1987 | McQueen | A01M 1/14 | 43/114 |
| 4,709,504 A * | 12/1987 | Andric | A01M 1/14 | 43/114 |
| 4,876,823 A * | 10/1989 | Brunetti | A01M 1/14 | 43/114 |
| 4,988,511 A | 1/1991 | Demetre | | |
| 4,998,376 A * | 3/1991 | Scherjbak | A01M 1/02 | 43/121 |
| 5,096,710 A * | 3/1992 | Minagawa | A01N 25/006 | 424/405 |
| 5,170,584 A * | 12/1992 | Perry | A01M 25/008 | 43/121 |
| 5,182,879 A * | 2/1993 | Hopkins | A01M 1/04 | 43/131 |
| 5,189,829 A * | 3/1993 | Johansson | A01M 1/14 | 43/114 |
| 5,273,761 A * | 12/1993 | Kim | A01N 25/006 | 424/84 |
| 5,300,293 A * | 4/1994 | Minagawa | A01N 25/006 | 424/405 |
| 5,346,700 A * | 9/1994 | Stapleton | A01N 25/006 | 424/409 |
| 5,454,186 A * | 10/1995 | Gang | A01M 1/14 | 43/114 |
| D377,961 S | 2/1997 | Dickson | | |
| 5,634,292 A * | 6/1997 | Kitterman | A01M 1/02 | 43/114 |
| 5,698,208 A * | 12/1997 | Nigg | A01N 59/14 | 424/405 |
| 5,705,176 A * | 1/1998 | Stapleton | A01N 25/006 | 424/409 |
| 5,915,948 A * | 6/1999 | Kunze | A01M 1/145 | 43/114 |
| 5,926,999 A * | 7/1999 | Vernon | A01G 1/08 | 43/121 |
| 5,930,944 A * | 8/1999 | Knuppel | A01M 1/026 | 43/114 |
| 6,007,832 A * | 12/1999 | Stapleton | A01N 25/006 | 424/409 |
| 6,202,339 B1 * | 3/2001 | Knuppel | A01M 1/026 | 43/114 |
| 6,266,917 B1 * | 7/2001 | Hight | A01M 1/103 | 43/114 |
| 6,618,983 B1 * | 9/2003 | Spragins | A01M 1/14 | 43/131 |
| 6,739,087 B2 | 5/2004 | Weiser | | |
| 6,789,352 B2 | 9/2004 | Price | | |
| 6,901,694 B1 * | 6/2005 | Neault | A01M 1/2011 | 43/131 |
| 6,910,300 B1 * | 6/2005 | Warren | A01M 25/004 | 43/131 |
| 7,987,629 B2 * | 8/2011 | Harper | A01M 25/004 | 43/131 |
| 8,104,223 B1 * | 1/2012 | Rodriguez | A01M 1/14 | 43/114 |
| 8,707,615 B2 * | 4/2014 | Cullen | A01M 29/34 | 43/121 |
| 9,173,388 B2 * | 11/2015 | Canfield | A01M 1/04 | |
| 2004/0057977 A1 * | 3/2004 | Gardner, Jr. | A01N 25/006 | 424/410 |
| 2007/0014826 A1 * | 1/2007 | Chan | A01N 25/006 | 424/410 |
| 2008/0289246 A1 * | 11/2008 | van Bers | A01M 1/14 | 43/114 |
| 2009/0288333 A1 * | 11/2009 | Johnston | A01M 1/02 | 43/114 |
| 2010/0297259 A1 * | 11/2010 | Wilson | A01N 43/22 | 424/635 |
| 2011/0088310 A1 * | 4/2011 | Parker | A01M 1/2011 | 43/131 |
| 2013/0174471 A1 * | 7/2013 | Vickery | A01M 25/004 | 43/131 |
| 2014/0170200 A1 * | 6/2014 | Ofek | A01N 25/00 | 424/417 |
| 2015/0007485 A1 * | 1/2015 | Hortel | A01M 1/023 | 43/114 |
| 2015/0007486 A1 * | 1/2015 | Backmark | A01M 1/2011 | 43/114 |
| 2015/0020438 A1 * | 1/2015 | Work | A01M 1/14 | 43/114 |
| 2015/0366210 A1 * | 12/2015 | Olson | A01M 1/026 | 43/114 |
| 2016/0106087 A1 * | 4/2016 | Ng | A01M 1/02 | 43/114 |
| 2016/0150775 A1 * | 6/2016 | Berengardt | A01N 25/008 | 424/489 |

FOREIGN PATENT DOCUMENTS

| | | | | |
|---|---|---|---|---|
| JP | 2002078438 A | * | 3/2002 | |
| JP | 2004016225 A | * | 1/2004 | |
| WO | 9115951 A | | 10/1991 | |
| WO | 9214358 A | | 9/1992 | |
| WO | WO 9502959 A1 | * | 2/1995 | A01M 1/2011 |

* cited by examiner

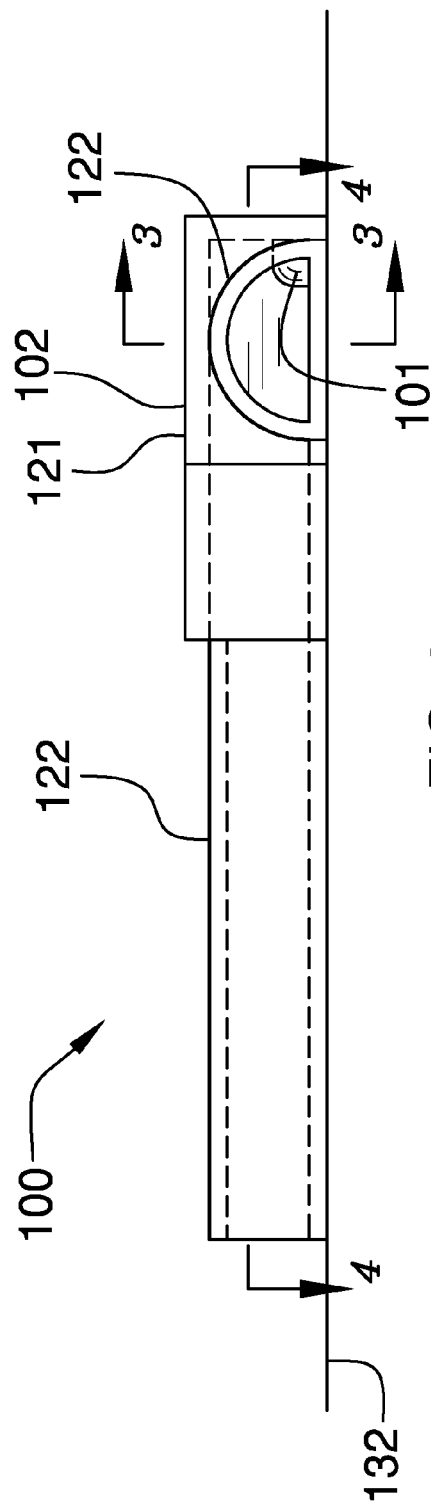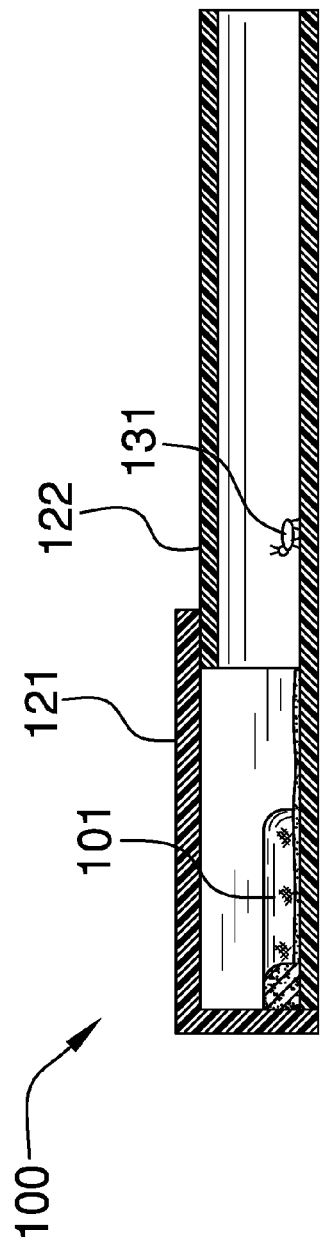

COCKROACH BAIT STATION

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of agriculture, more specifically, a pest repellant characterized by its form or non-active ingredient.

SUMMARY OF INVENTION

The cockroach bait station is an eradication system that is adapted for use with cockroaches. The cockroach bait station is comprises a bait and a bait station. The bait is a high energy, and therefore highly attractive, bait source that is laced with a poison that is known to be effective in: 1) limiting the future activities of cockroaches after ingestion; and, 2) is readily shared and transferred within a community of cockroaches.

These together with additional objects, features and advantages of the cockroach bait station will be readily apparent to those of ordinary skill in the art upon reading the following detailed description of the presently preferred, but nonetheless illustrative, embodiments when taken in conjunction with the accompanying drawings.

In this respect, before explaining the current embodiments of the cockroach bait station in detail, it is to be understood that the cockroach bait station is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the cockroach bait station.

It is therefore important that the claims be regarded as including such equivalent construction insofar as they do not depart from the spirit and scope of the cockroach bait station. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 2 is a side view of an embodiment of the disclosure.

FIG. 3 is a cross-sectional view of an embodiment of the disclosure across 3-3 as shown in FIG. 2.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
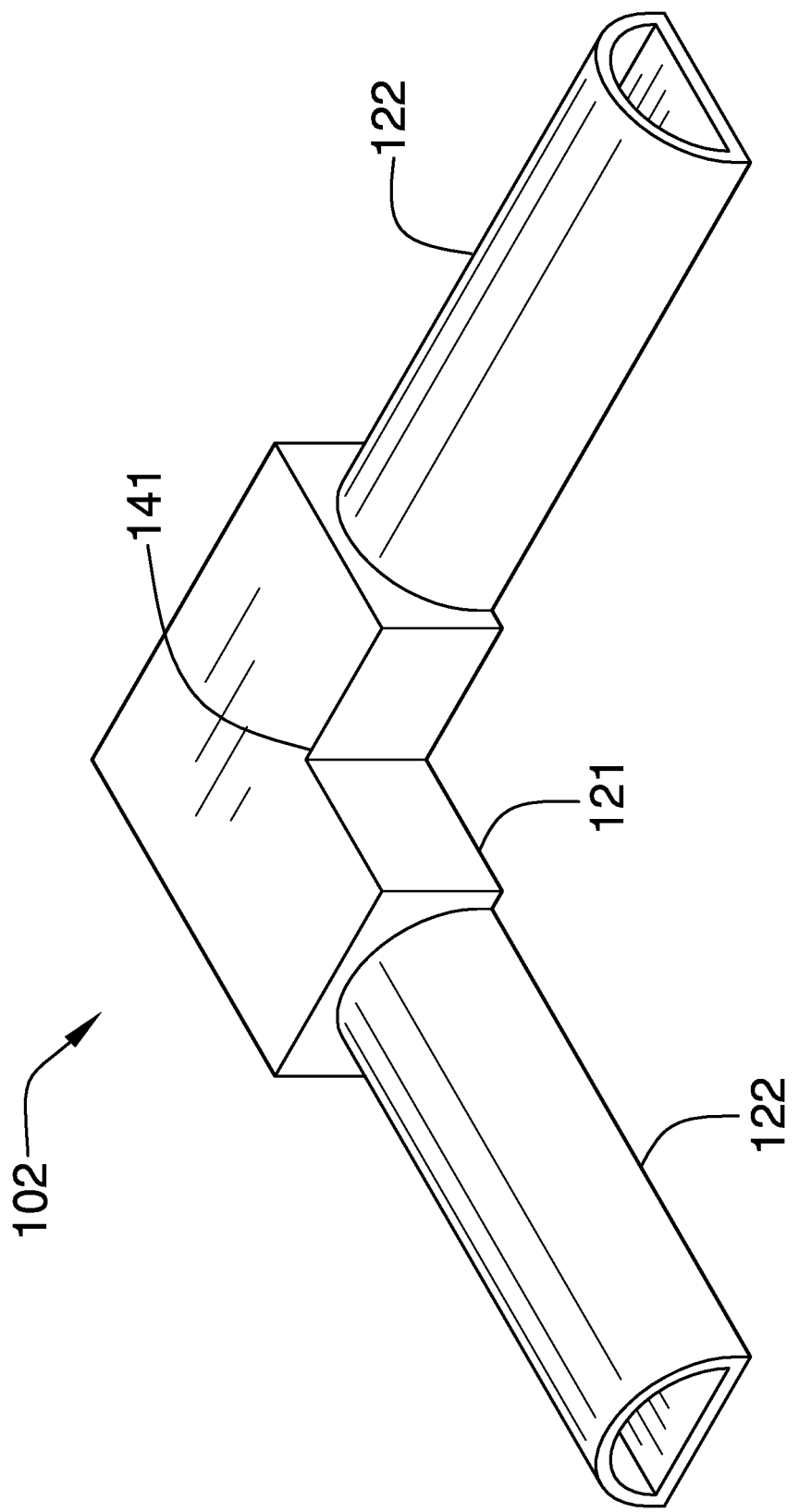
FIG. 1 is a perspective view of an embodiment of the disclosure.
Figure 4:
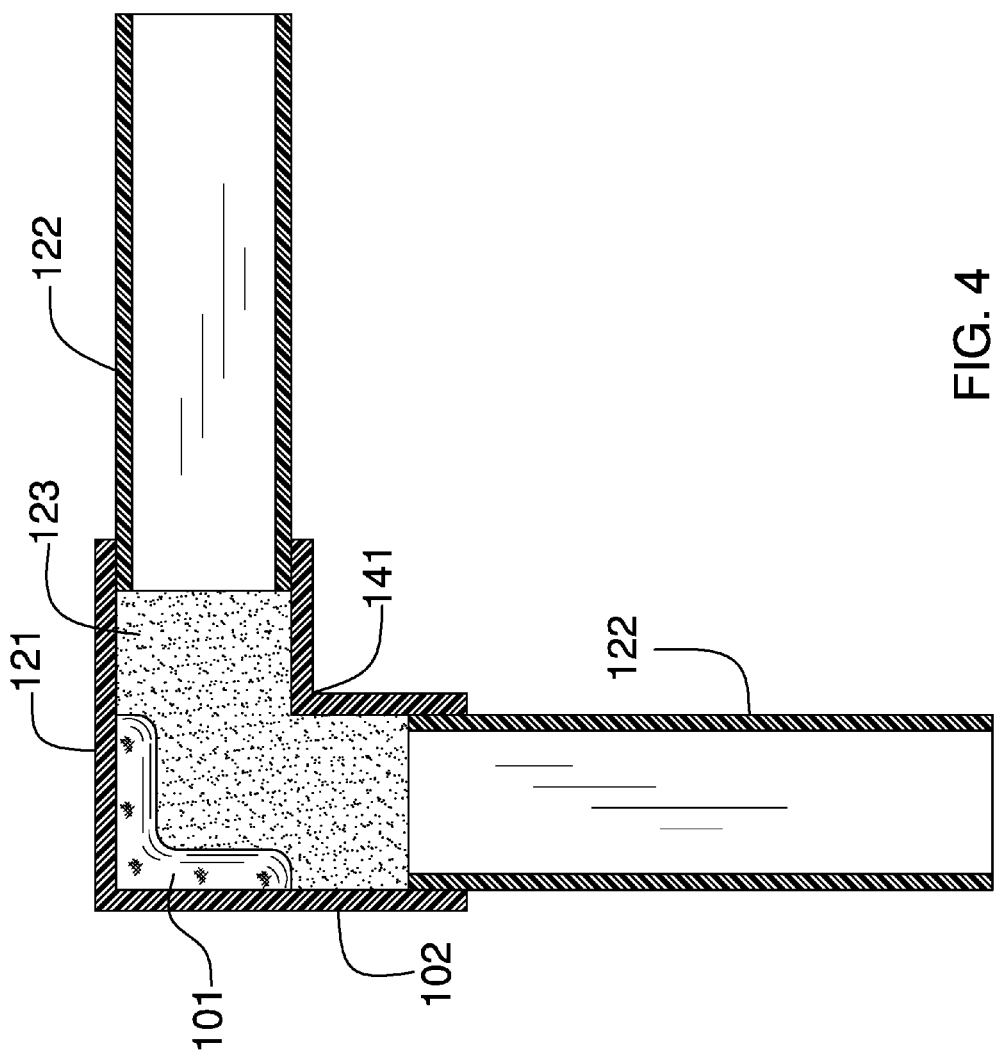
FIG. 4 is a cross-sectional view of an embodiment of the disclosure across 4-4 as shown in FIG. 2.
Figure 5:
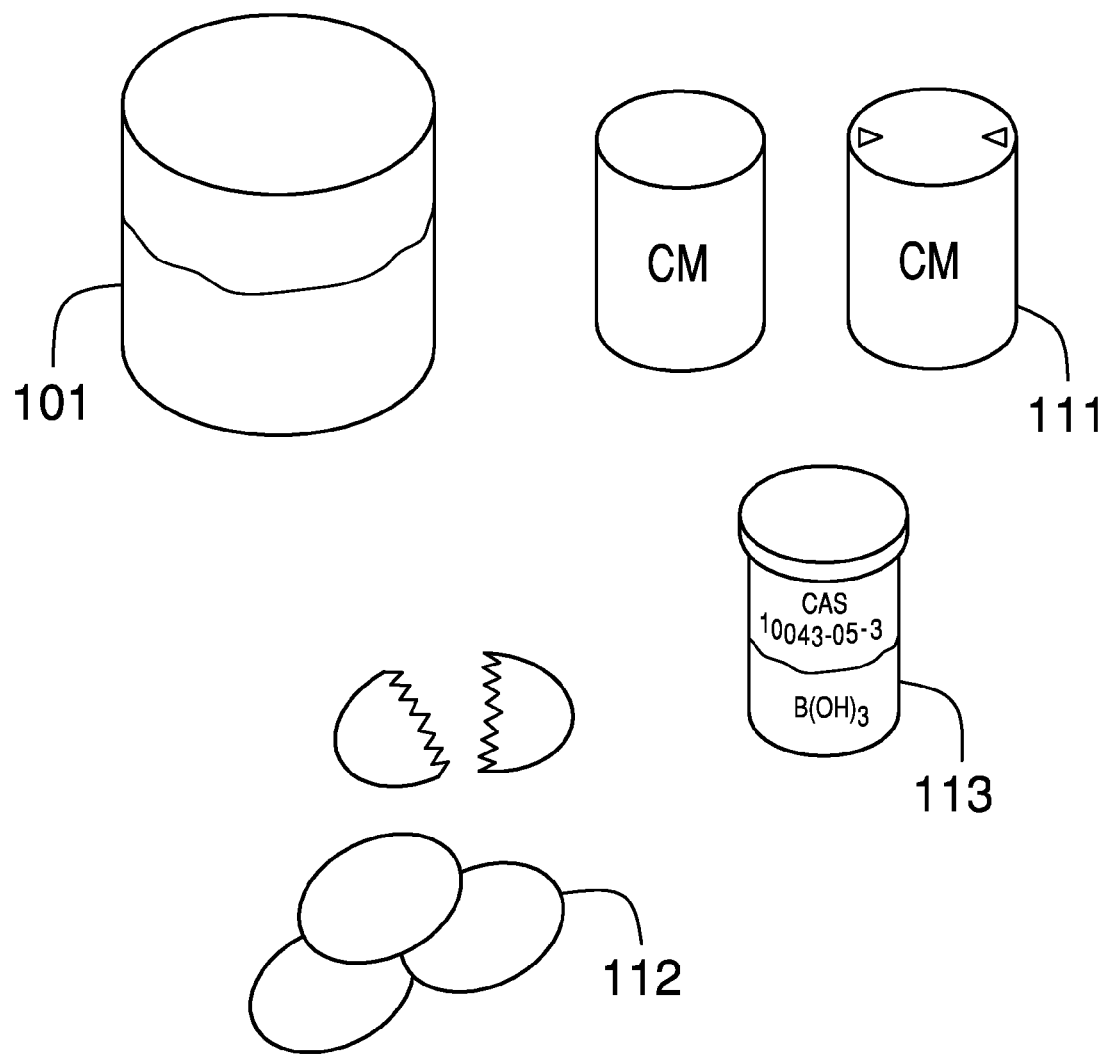
FIG. 5 is a detail view of an embodiment of the disclosure.

Detailed reference will now be made to one or more potential embodiments of the disclosure, which are illustrated in FIGS. 1 through 5.

The cockroach bait station 100 (hereinafter invention) is comprises a bait 101 and a bait station 102. The invention 100 is an eradication system that is adapted for use with a cockroach 131. The bait 101 emulates a high energy, and therefore highly attractive, food source that is laced with an active substance that is known to be effective in: 1) limiting the future activities of a cockroach 131 after ingestion; and, 2) is readily shared and transferred within a community of cockroaches 131.

The bait 101 comprises a mixture of condensed milk 111, eggs 112, and boric acid 113. The bait 101 has a gel like form of adequate viscosity such that the bait 101 can be treated and stored as if it were a solid. It is explicitly recognized within this disclosure, that the bait 101 described is not strictly a gel but also comprises components of an emulsion or a viscous emulsion. These emulsion components will be included within the use of the term gel within this disclosure. This is done for the purposes of simplicity and for clarity of exposition of the disclosure and is not intended to limit the scope of the appended claims. Those skilled in the art will recognize that the innovations described in this disclosure can be readily modified to accommodate the inclusion or exclusion of the emulsion or the viscous emulsion components with a minimum of modification and experimentation.

The boric acid 113 is the active substance described above. The use of boric acid 113 is preferred because of: 1) its effectiveness against a cockroach 131; and, 2) the high tolerance of mammals of exposure to and ingestion of boric acid 113.

The proportion of egg 112 within the bait 101 mixture is between 25% and 35% (m/m) inclusive. The proportion of condensed milk 111 within the bait 101 mixture is between 40% and 65% (m/m) inclusive. The proportion of boric acid 113 within the bait 101 mixture is between 5% and 35% (m/m) inclusive. The egg 112 is selected from the group consisting of chicken egg, duck egg, quail egg, or ostrich egg. Chicken eggs are preferred for cost effectiveness. Ostrich eggs are preferred for production efficiency. Duck eggs are preferred for nutritional attractiveness. The condensed milk 111 is a readily and commercially available food stuff. The boric acid 113 is readily and commercially available. Boric acid 113, also referred to a hydrogen borate, has a chemical formula of $B(OH)_3$. The CAS Registry number for boric acid 113 is 10043-35-3.

In the first potential embodiment of the disclosure, the bait 101 is formed as described in this paragraph. The egg 112 and the condensed milk 111 are mixed until smooth. The boric acid 113 is then incorporated into the mixture. The mixture is baked at a baking temperature of less than 150 C until the temperature of the mixture reaches a minimum mixture temperature of 75 C. It is anticipated that the bake time will be approximately 45 minutes. It is preferred that the mixture be baked in a water bath. It is preferred that the baking temperature be set such that the mixture requires at least 30 minutes of baking before the mixture reaches the minimum temperature.

In a second potential embodiment of the disclosure, the bait 101 mixture further comprises food coloring elements that increase the intensity of the wavelengths of the light reflected by the bait 101 that are less than 570 nm relative to other wavelengths. The purpose of this adjustment is to move the color of the bait 101 away from the red portion (defined as light greater than 570 nm) of the color spectrum. This color adjustment makes the bait 101 more visible to the cockroach 131.

The bait 101 is distributed to the cockroach 131 through the bait station 102. The bait station 102 comprises a bait housing 121, a plurality of passages 122, and an adhesive 123. As shown most clearly in FIGS. 1 and 4, the bait housing 121 is a hollow rectilinear block structure that is formed in an L shape 141. The purpose of the L shape 141 is to: 1) allow the bait housing 121 to be readily placed in a corner; and, 2) to route the cockroach 131 directly towards the bait 101. A rectilinear L shape 141 block is preferred to a rectangular block to prevent a cockroach 131 from "cutting the corner" and missing the bait 101.

The plurality of passages 122 are the entrances into the bait station 102. Each of the plurality of passages 122 is a hollow semi-cylindrical structure. As shown most clearly in FIG. 4, each of the plurality of passages 122 is attached to the end of an arm of the L shape 141 of the bait housing 121 that is distal from the vertex formed by the intersection of the two arms of the L shaped 141 structure. Each of the plurality of passages 122 forms an aperture through which the cockroach 131 can enter. The purpose of each of the plurality of passages 122 is to create a dark region into which a cockroach 131 is willing to enter and through which the cockroach 131 is comfortable to travel.

The bait station 102 is placed upon a supporting surface 132. The interior surface of the bait housing 121 that is proximal to the supporting surface 132 is coated in an adhesive 123. The purpose of the adhesive 123 is to: 1) hold the bait 101 in position within the bait station 102; and, 2) to capture one or more cockroaches 131 within the bait housing 121.

To use the invention 100, the invention 100 is placed in the corner of a location likely to be frequented by a cockroach 131.

In the first potential embodiment of the disclosure, the bait station 102 is formed from two pieces of molded plastic, which are designed to "snap" together after the bait station 102 has been treated with the adhesive 123 and loaded with the bait 101. The adhesive 123 is a pressure sensitive adhesive.

The following definitions were used in this disclosure:

Adhesive: As used in this disclosure, an adhesive is a chemical substance that can be used to adhere two or more objects to each other. Types of adhesives include, but are not limited to, epoxies, polyurethanes, polyimides, or cyanoacrylates, silicone, or latex based adhesives.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or cone like structure. When the center axes of two cylinder or like structures share the same line they are said to be aligned. When the center axes of two cylinder like structures do not share the same line they are said to be offset.

Cylinder: As used in this disclosure, a cylinder is a geometric structure defined by two identical flat and parallel ends, also commonly referred to as bases, which are circular in shape and connected with a single curved surface, referred to in this disclosure as the face. The cross section of the cylinder remains the same from one end to another. The axis of the cylinder is formed by the straight line that connects the center of each of the two identical flat and parallel ends of the cylinder. In this disclosure, the term cylinder specifically means a right cylinder, which is defined as a cylinder wherein the curved surface perpendicularly intersects with the two identical flat and parallel ends.

Emulsion: As used in this disclosure, an emulsion is a dispersion of droplets or miscelles of a first liquid in a second liquid in which the first liquid and second liquid are not soluble or miscible.

Exterior: As used in this disclosure, the exterior is use as a relational term that implies that an object is not contained within the boundary of a structure or a space.

Gel: As used in this disclosure, a gel is a substance comprising mostly of liquid (by mass) that is trapped in a cross-linked network of proteins and peptides that exhibits the properties of a solid.

Interior: As used in this disclosure, the interior is use as a relational term that implies that an object is contained within the boundary of a structure or a space.

Rectilinear: As used in this disclosure, rectilinear is an adjective that is used to describe an object that: 1) moves in a straight line or lines; 2) consists of a straight line or lines; 3) is bounded by a straight line or lines; or, 4) is otherwise characterized by a straight line or lines.

Semi-Cylinder: As used in this disclosure, a semi-cylinder is half of a cylinder that is divided lengthwise such that the center axis of the cylinder is fully contained within the dividing plane.

Viscosity: As used in this disclosure, viscosity refers to the resistance of a liquid or an elastic material to deformation. Higher viscosity would refer to a greater resistance to flow or to deformation.

Viscous Emulsion: As used in this disclosure, a viscous emulsion is an emulsion where the viscosity or flow rate of the emulsion is such that the emulsion can for all practical purposes be treated and contained as if it were a solid. In common usages, a viscous emulsions is often referred to as a cream.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. An eradication system comprising:
   a bait and a bait station;
   wherein the eradication system is adapted for use with a cockroach;
   wherein the bait is stored in the bait station;
   wherein the bait emulates a food source that is laced with an active substance;
   wherein the active substance limits future activities of the cockroach after ingestion;
   wherein the active substance is readily shared and transferred within a community of cockroaches;
   wherein boric acid is the active substance;
   wherein the bait comprises a mixture of condensed milk, egg, and the boric acid;
   wherein the bait can be treated and stored as a solid;
   wherein a proportion of the boric acid within the bait mixture is between 5% and 35% (m/m) inclusive;
   wherein a proportion of the egg within the bait mixture is between 25% and 35% (m/m) inclusive;
   wherein a proportion of the condensed milk within the bait mixture is between 40% and 65% (m/m) inclusive;
   wherein the bait mixture further comprises a food coloring;
   wherein the food coloring increases an intensity of wavelengths of light reflected by the bait which are less than 570 nm relative to other wavelengths of light reflected from the bait;
   wherein the bait is distributed to the cockroach through the bait station;
   wherein the bait station comprises a bait housing, a plurality of passages, and an adhesive;
   wherein the plurality of passages are attached to the bait housing;
   wherein the adhesive is applied in an interior of the bait housing;
   wherein the bait housing is a hollow rectilinear block structure that is formed in an L shape, the L shape of the bait housing formed by two arms intersecting at a vertex;
   wherein each of the plurality of passages forms an aperture through which the cockroach can enter the bait station;
   wherein each of the plurality of passages is a hollow semi-cylindrical structure;
   wherein each of the plurality of passages is attached to a respective end of one of the arms of the L shape of the bait housing that is distal from the vertex of the L shape of the bait housing;
   wherein each of the plurality of passages is provided to create a dark region.

2. The eradication system according to claim 1 wherein an interior surface of the interior of the bait housing that is proximal to a supporting surface is coated with the adhesive.

3. The eradication system according to claim 2 wherein the adhesive is a pressure sensitive adhesive.

4. The eradication system according to claim 2 wherein the egg is a duck egg.

5. The eradication system according to claim 2 wherein the egg is an ostrich egg.

6. The eradication system according to claim 1
   wherein the egg and the condensed milk are mixed until smooth;
   wherein the boric acid is incorporated into the mixture;
   wherein the mixture is baked at a baking temperature of less than 150° C. until a temperature of the mixture reaches a minimum temperature of 75° C.

7. The eradication system according to claim 6 wherein an interior surface of the interior of the bait housing that is proximal to a supporting surface is coated with the adhesive.

8. The eradication system according to claim 6 wherein the egg is selected from the group consisting of duck egg, ostrich egg, or quail egg.

9. The eradication system according to claim 8 wherein an interior surface of the interior of the bait housing that is proximal to a supporting surface is coated with the adhesive.

10. The eradication system according to claim 9 wherein the adhesive is a pressure sensitive adhesive.

* * * * *